United States Patent [19]

Matsumoto et al.

[11] Patent Number: 5,660,179
[45] Date of Patent: Aug. 26, 1997

[54] ULTRASONIC DIAGNOSTIC APPARATUS

[75] Inventors: Kazuhiro Matsumoto; Etsuro Machida, both of Kawasaki, Japan

[73] Assignee: Fujitsu Limited, Kawasaki, Japan

[21] Appl. No.: 552,257

[22] Filed: Nov. 2, 1995

[30] Foreign Application Priority Data

Apr. 18, 1995 [JP] Japan ................................. 7-092657

[51] Int. Cl.$^6$ ................................................ A61B 8/00
[52] U.S. Cl. ........................................... 128/660.04
[58] Field of Search ..................... 128/660.01, 660.04, 128/660.07, 661.01, 661.09

[56] References Cited

U.S. PATENT DOCUMENTS

| | | | |
|---|---|---|---|
| 5,181,513 | 1/1993 | Touboul et al. | 128/660.07 |
| 5,184,622 | 2/1993 | Tomura | 128/660.07 |
| 5,186,176 | 2/1993 | Hiki et al. | 128/660.04 X |
| 5,211,167 | 5/1993 | Amenomori | 128/662.06 |
| 5,345,938 | 9/1994 | Nishiki et al. | 128/662.06 X |
| 5,415,167 | 5/1995 | Wilk | 128/660.07 X |
| 5,497,776 | 3/1996 | Yamazaki et al. | 128/662.06 X |

*Primary Examiner*—Francis Jaworski
*Attorney, Agent, or Firm*—Staas & Halsey

[57] ABSTRACT

There is provided an ultrasonic diagnostic apparatus in which ultrasonic waves are transmitted into the subject to obtain received signals through receiving the ultrasonic waves reflected within the subject, thereby displaying an image based on the received signals. In the ultrasonic diagnostic apparatus, a plurality of images, for instance, a normal diagnostic image case and abnormal diagnostic image cases are stored beforehand in the image memory corresponding to kinds of body mark and positions of probe mark, and images are displayed in accordance with the designated kind of body mark and position of probe mark. This feature permits even an operator not skilled in the operation to perform accurately and readily estimation of the tomographic image displayed on the display screen through operation by himself.

7 Claims, 5 Drawing Sheets

Fig. 2

| BODY MARKS | PROBE MARK COORDINATES | | | IMAGE ADDRESSES | | | | | | |
|---|---|---|---|---|---|---|---|---|---|---|
| | x | y | θ | 0 | 1 | 2 | 3 | 4 | 5 | ... |
| BODY MARK PATTERN 0 | x0 | y0 | θ0 | A0 | A1 | A2 | A3 | A4 | A5 | ... |
| | x0 | y0 | θ1 | B0 | B1 | B2 | B3 | B4 | B5 | ... |
| | x0 | y0 | θ2 | C0 | C1 | C2 | C3 | C4 | C5 | ... |
| | X1 | Y1 | θ0 | D0 | D1 | D2 | D3 | D4 | D5 | ... |
| | X1 | Y1 | θ1 | E0 | E1 | E2 | E3 | E4 | E5 | ... |
| | . | . | . | . | . | . | . | . | . | ... |
| BODY MARK PATTERN 1 | x00 | y00 | θ00 | A00 | A11 | A22 | A33 | A44 | A55 | ... |
| | x00 | y00 | θ11 | B00 | B11 | B22 | B33 | B44 | B55 | ... |
| | x00 | y00 | θ22 | C00 | C11 | C22 | C33 | C44 | C55 | ... |
| | X11 | Y11 | θ00 | D00 | D11 | D22 | D33 | D44 | D55 | ... |
| | X11 | Y11 | θ11 | E00 | E11 | E22 | E33 | E44 | E55 | ... |
| | . | . | . | . | . | . | . | . | . | ... |

ULTRASONIC DIAGNOSTIC APPARATUS

BACKGROUND OF THE INVENTION

1. Field of the Invention

The present invention relates to an ultrasonic diagnostic apparatus in which ultrasonic waves are transmitted into the subject to obtain received signals through receiving the ultrasonic waves reflected within the subject, thereby displaying an image based on the received signals.

2. Description of the Related Art

Hitherto, there has been used an ultrasonic diagnostic apparatus in which ultrasonic waves are transmitted toward the subject, especially a living body, ultrasonic waves reflecting from a tissue within the living body are received to generate received signals, and a tomographic image of the living body is displayed on the basis of the received signals, thereby facilitating a diagnostic of diseases of the viscus inner organ or the like in the living body.

FIG. 7 is a typical illustration showing the state of operations of an ultrasonic diagnostic apparatus.

Usually, an ultrasonic diagnostic apparatus is arranged, for the convenience of handling, in such a manner that a probe 2 is connected to a main body 1 when it is used. As shown in FIG. 7, an operator 3 puts a tip portion 2a of the probe 2 upon the subject 4, and controls a position and an angle of the tip portion 2a. The tip portion 2a incorporates thereinto an ultrasonic probe (not illustrated) for transmitting and receiving ultrasonic waves. The ultrasonic probe transmits ultrasonic waves toward the inside of the subject 4 and receives the ultrasonic waves reflected within the subject 4. The received signals thus received are fed through a cable 2b of the probe 2 and a connector 2c for connecting the probe 2 with the main body 1 to the main body 1.

Inside the main body 1, the received signals are subjected to a processing according to an operation and the like of an operation panel 80 by the operator 3, so that a tomographic image within the subject 4 is displayed, based on the processed received signals, on a display screen 70a of a display unit 70.

In the display of tomographic images on the display screen 70a, it may be difficult to see which diagnostic site or internal organ of the subject 4 is displayed and from which position and direction is the subject 4 irradiated with ultrasonic waves to obtain the tomographic image. Thus, there is an ultrasonic diagnostic apparatus in which a body mark indicating as to which diagnostic site or internal organ of the subject 4 is a diagnostic object through making a design thereof, and a probe mark indicating a relative position relation between the diagnostic site or internal organ and the tip portion 2a of the probe 2 are able to be displayed through an operation of the operation panel 80 by the operator 3.

A display of the body mark and the probe mark together with the tomographic image within the subject 4 makes it possible to provide a display easy to see as to how and upon which diagnostic site or internal organs the tip portion 2a of the probe 2 is put. However, it will be difficult for a beginner to discriminate among a normal image indicating that the tomographic image thus obtained involves no lesion or diseases, an abnormal image indicating that the tomographic image involves lesion or diseases, and an abnormal image indicating as to what lesion or diseases the tomographic image is involved in. Thus, it is necessary for an operator to refer to, for example diagnostic cases collecting the related photographs. This involves such a problem that it takes much times for determination as to whether the tomographic image displayed on the display screen is good or bad.

SUMMARY OF THE INVENTION

In view of the foregoing, it is therefore an object of the present invention to provide an ultrasonic diagnostic apparatus permitting even an operator not skilled in the operation to perform accurately and readily estimation of the tomographic image displayed on the display screen through operation by himself.

To achieve the above-mentioned objects, according to the present invention, there is provided an ultrasonic diagnostic apparatus comprising a probe for transmitting ultrasonic waves inside a subject and receiving the ultrasonic waves reflected within the subject, and display means for displaying an image inside the subject on the basis of received signals obtained through receiving of the ultrasonic waves by said probe, said ultrasonic diagnostic apparatus further comprising: an operation panel for designating a plurality of kinds of body marks each indicative of a diagnostic site or an internal organs of interest and in addition for designating a position of a probe mark indicative of a position of the probe to be put upon the subject; and memory means adapted to detachably or fixedly mounting thereon an image memory for storing a plurality of image data representative of a plurality of images corresponding to kinds of the body mark and positions of the probe mark, wherein said display means displays an image based on the received signals and an image based on the image data stored in said image memory corresponding to the kinds of the body mark and the positions of the probe mark, which are designated through an operation of said operation panel.

In the above-mentioned apparatus, it is preferable that said display means simultaneously displays the body mark and the probe mark, which are designated through an operation of said operation panel, and the image based on the image data stored in said image memory corresponding to the kinds of the body mark and the positions of the probe mark, which are designated through an operation of said operation panel. In this case, it is acceptable that said display means simultaneously displays the image based on the received signals, the body mark and the probe mark, which are designated through an operation of said operation panel, and the image based on the image data stored in said image memory corresponding to the kinds of the body mark and the positions of the probe mark, which are designated through an operation of said operation panel.

Further, in the above-mentioned apparatus, it is preferable that when the position of the probe mark is altered, during a display of the image based on the image data by said display means, through an operation of the operation panel, said display means displays the image based on the image data stored in said image memory corresponding to the position of the probe mark after the alteration, instead of the image based on the image data which is involved in the preceding display.

Incidentally, it is acceptable that the "image memory" referenced in the present invention may be a fixed type of storage media such as a hard disk incorporated into the apparatus, a network drive available to access through a network, etc., alternatively, a detachable storage media such as a floppy disk, a CDROM, an optical disk, an optical magnetic disk, etc. Further, it is noted that the "position" of the probe referenced in the present invention may include an "angle".

According to the ultrasonic diagnostic apparatus of the present invention, a plurality of images, for instance, a normal diagnostic image case and abnormal diagnostic image cases are stored beforehand in the image memory corresponding to kinds of body mark and positions of probe mark, and images are displayed in accordance with the designated kind of body mark and position of probe mark. This feature permits even an operator not skilled in the operation to perform accurately and readily estimation of the tomographic image displayed on the display screen through operation by himself.

The simultaneous display of the image stored in the image memory and the body mark and the probe mark makes it possible to visibly know how and which diagnostic site or internal organs the probe is put upon. Thus, it is possible to provide an apparatus which is excellent in operational efficiency. Further, if the tomographic image of the subject now on diagnosis is simultaneously in addition displayed, it makes it more easy to compare image-to-image with each other. The movement of the probe by an operator will involve the change of the tomographic image of the subject. In this case, when the operator inputs through the operation panel a position after the movement of probe, the image corresponding to the probe mark after the alteration is displayed instead of the image read out of the image memory which image is involved in the preceding display. This feature makes it possible to easily compare the tomographic image of the subject, while the position of the probe is changed, with the associated diagnostic image cases read out of the image memory.

BRIEF DESCRIPTION OF THE DRAWINGS

FIG. 2 is a typical illustration showing a management table within the image memory 110 shown in FIG. 1;

DESCRIPTION OF THE PREFERRED EMBODIMENTS

Hereinafter, there will be described embodiments of the present invention.

Figure 1:
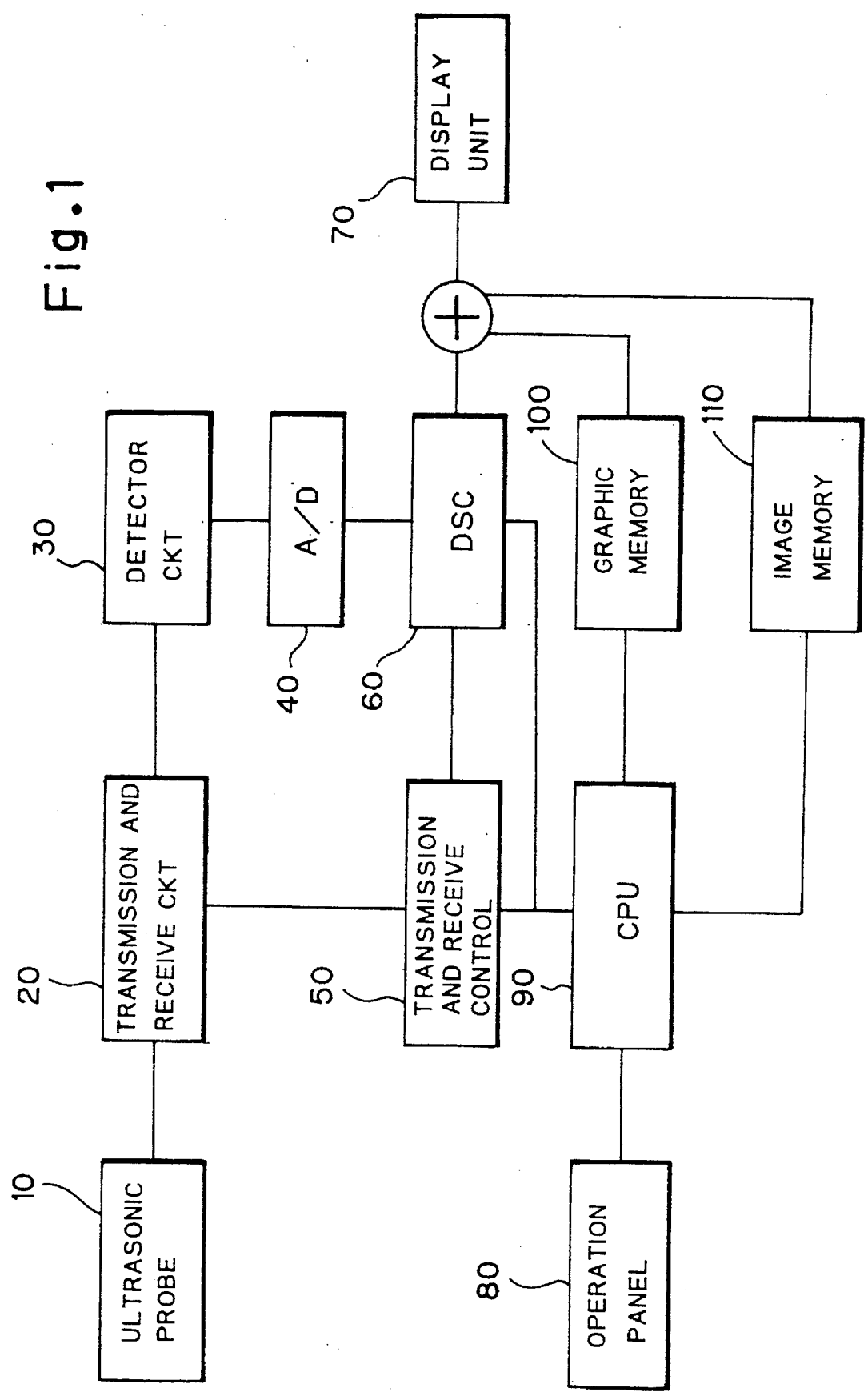
FIG. 1 is a block diagram showing the basic arrangement of constituents of an ultrasonic diagnostic apparatus according to the present invention.

FIG. 1 is a block diagram showing the basic arrangement of constituents of an ultrasonic diagnostic apparatus according to the present invention. In the following figures, the same parts are denoted by the same reference numbers as those of FIG. 1.

Figure 7:
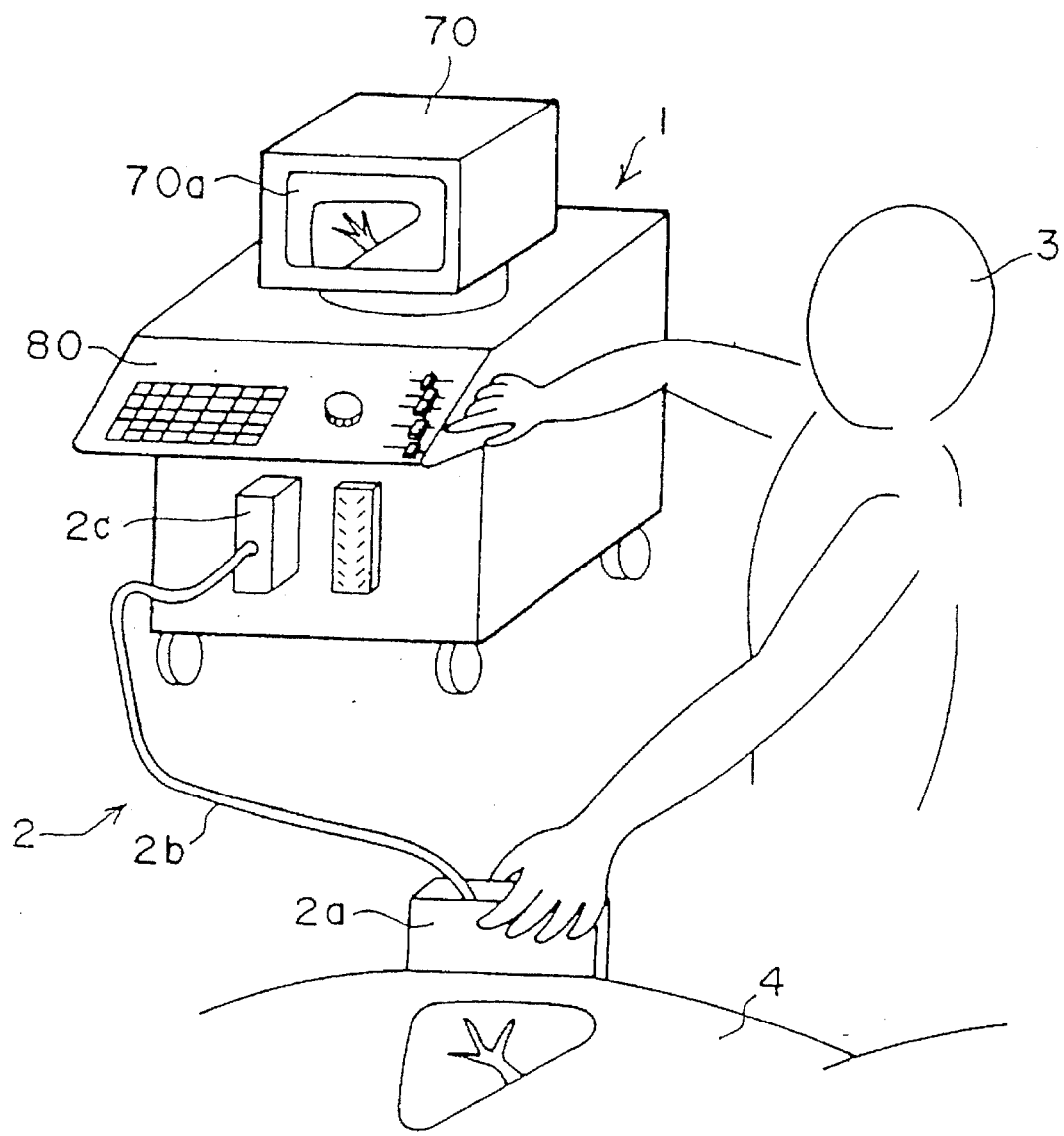
FIG. 7 is a typical illustration showing the state of operations of an ultrasonic diagnostic apparatus.

According to the embodiment shown in FIG. 1, an ultrasonic probe 10 is disposed on the tip portion 2a of the probe 2 shown in FIG. 7. The ultrasonic probe 10 comprises a plurality of arranged ultrasonic transducers.

A transmission and receive control circuit 50 controls a transmission and receive circuit 20 in accordance with an instruction of a CPU 90, so that the transmission and receive circuit 20 supplies high voltage pulses in associated timings controlled to the plurality of ultrasonic transducers constituting the ultrasonic probe 10. Upon receipt of the high voltage pulses, the respective ultrasonic transducers transmit ultrasonic waves toward the inside of the subject so as to form a predetermined transmission beam within the subject. The ultrasonic waves reflected within the subject and returned to the ultrasonic probe 10 are received by the plurality of ultrasonic transducers constituting the ultrasonic probe 10 and converted into a plurality of received signals. The transmission and receive circuit 20 is controlled in accordance with the transmission and receive control circuit 50 so that the received signals thus obtained are beamformed to form a receive beam having a focal point at a predetermined depth position within the subject.

Thereafter, the beamformed received signals are fed to a detector circuit 30 to be subjected to an amplitude detection. The received signals subjected to the amplitude detection are converted into digital signals by an A/D converter 40 and then applied to a digital scan converter (DSC) 60. The above-mentioned operation is repeatedly carried out in such a manner that transmission and receive beams of ultrasonic waves are formed in various directions within a certain tomographic plane of the inside of the subject, thereby obtaining a tomographic image on the tomographic plane.

The digital scan converter (DSC) 60 serves as a circuit for converting the received digital signals into signals adapted to a display on a display unit 70. The signals converted for use in display are applied to the display unit 70 in which a tomographic image within the subject is displayed on the display screen 70a (FIG. 7).

An operation of the operation panel 80 by an operator permits an entry of information as to a display of a body mark indication, kinds of body mark and positions (including angles) of a probe mark. When the CPU 90 received these kinds of information, the associated body mark is read out of a graphic memory 100 and is transmitted together with a default position of the probe mark to the display unit 70, so that the body mark and probe mark are displayed on the display screen 70a. At that time, the CPU 90 retrieves an address from the management table within an image memory 110 on the basis of the selected kind of body mark and position of probe mark to read out the associated diagnostic image case from the data base within the image memory 110. The diagnostic image case thus read is transferred to the display unit 70. Thus, the diagnostic image case read out of the image memory 110 is also displayed on the display screen 70a of the display unit 70.

Figure 3:
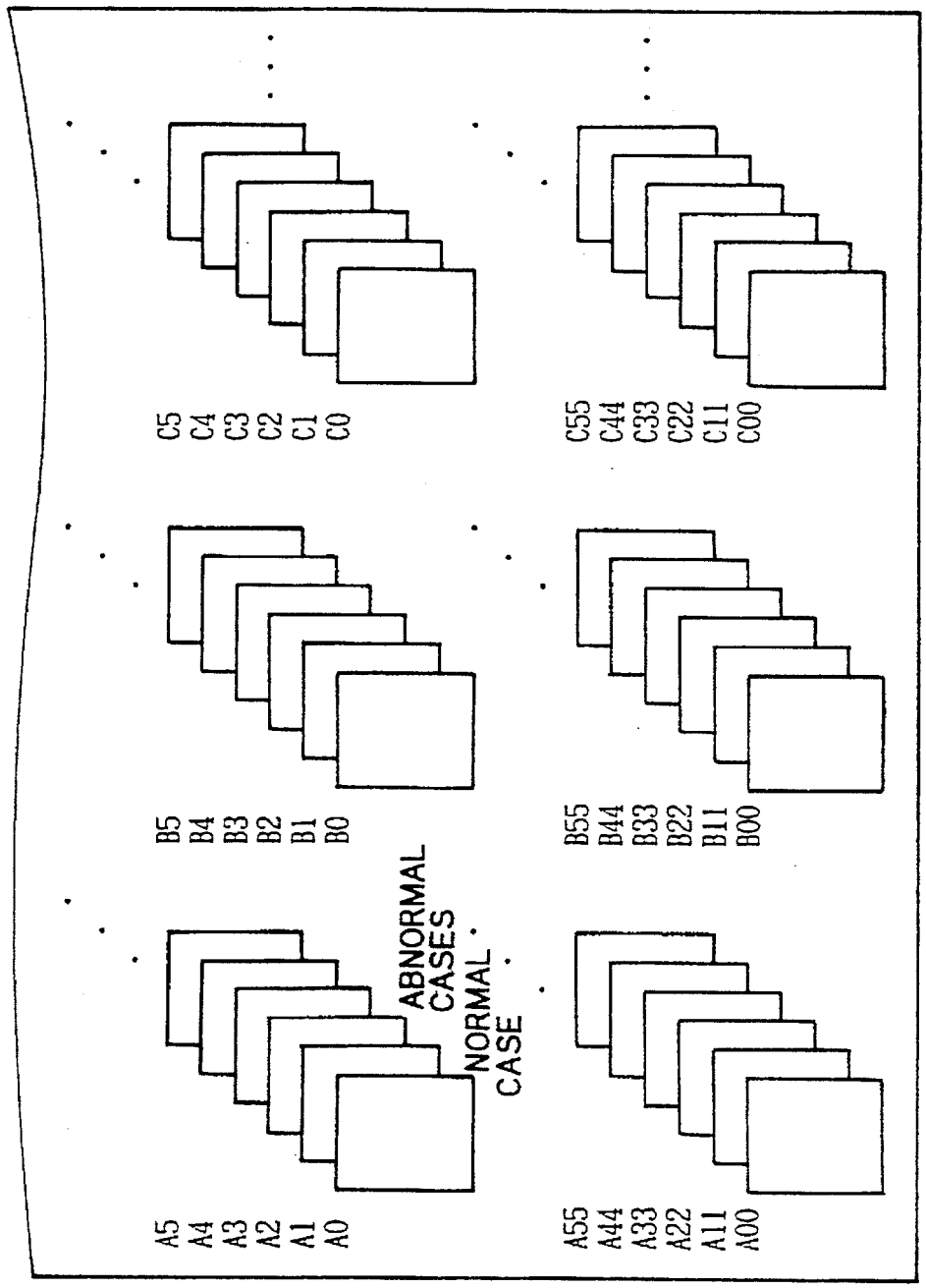
FIG. 3 is a typical illustration showing a data base within the image memory 110 shown in FIG. 1.

FIG. 2 is a typical illustration showing a management table within the image memory 110 shown in FIG. 1. FIG. 3 is a typical illustration showing a data base within the image memory 110 Shown in FIG. 1.

As shown in FIG. 2, the management table within the image memory 110 stores storage addresses of images corresponding to kinds of body mark and positions (x, y, θ) of probe mark. Further, as shown in FIG. 3, the data base within the image memory 110 stores normal diagnostic image cases and abnormal diagnostic image cases corresponding to the respective addresses. According to the present embodiment, to a single combination of a kind of body mark and a position of probe mark, a normal case is stored in the first address and an abnormal case is stored in each of the second address et seqq.

As described above, a designation of a kind of body mark and a position of probe mark through an operation of the operation panel 80 allows an image (normal case) of the associated first address in the data base to be displayed. And an instruction of change over of the diagnostic image through the operation panel 80 permits the image (abnormal case) of the subsequent address to be sequentially displayed.

For instance, in a case where a pattern of the body mark is '0' and a position of the probe is (X0, Y0, θ0), first, an image (normal case) of an address A0 is read out of the data base and then displayed. Subsequently, when the CPU received a command for switching of the diagnostic image from the operation panel 80, an image (abnormal case) of an address A1 is displayed, instead of the image of the address A0. Incidentally, according to the present invention, while the first image is of a normal case and the second image et seqq. are each of an abnormal image for each combination of a kind of body mark and a position of probe, it is not restricted in the sequence of images.

Next, in the state that the body mark is displayed, when the CPU 90 received a command for movement of a probe position from the operation panel 80, the position of the probe mark now displayed is shifted to a position after the movement. At that time, the CPU 90 retrieves an address of the associated image from the management table (FIG. 2) within the image memory 110 on the basis of the body mark now displayed and a position of probe mark after altered, so that the associated diagnostic image case within the data base (FIG. 3) is displayed on the display unit 70. In a similar fashion to that of the above-mentioned matter, when the CPU 90 received the command for switching the diagnostic image from the operation panel 80, the subsequent diagnostic image case is displayed.

Incidentally, when a position of the probe mark is moved, if the management table has no data corresponding to the position of the probe mark after movement, one or a plurality of data, which are near in angle, involved in the designated body mark are selected. In a case where a plurality of data are selected, straight line lengths of XY coordinates are compared with each other, and an image within the data base, which image is associated with the address of the nearest one, is displayed.

Figure 4:
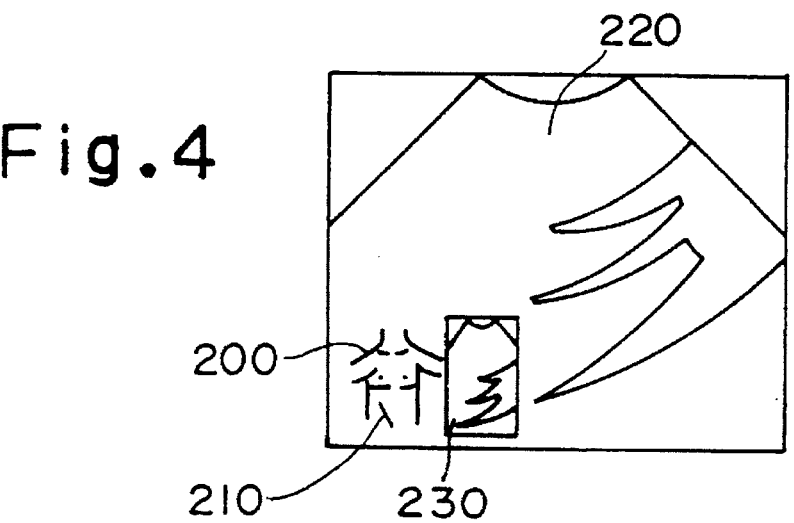
FIG. 4 is a view showing an example of a display on a display screen of a display unit.
Figure 5:
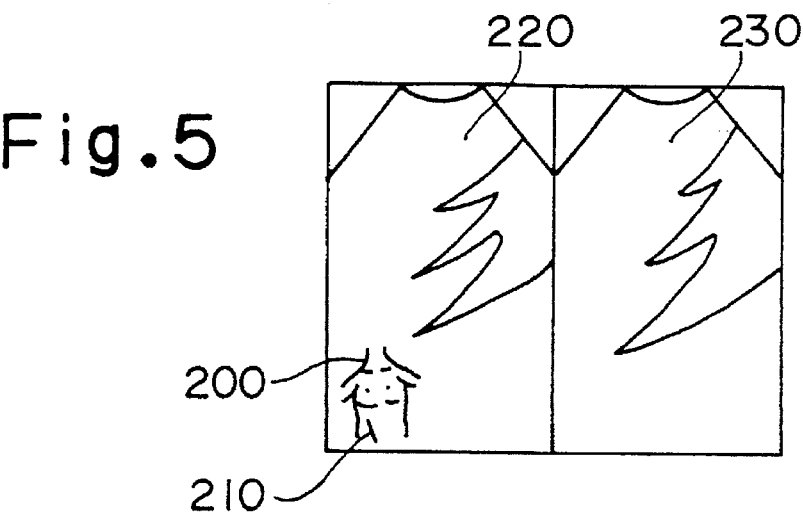
FIG. 5 is a view showing another example of a display on a display screen of a display unit.
Figure 6:
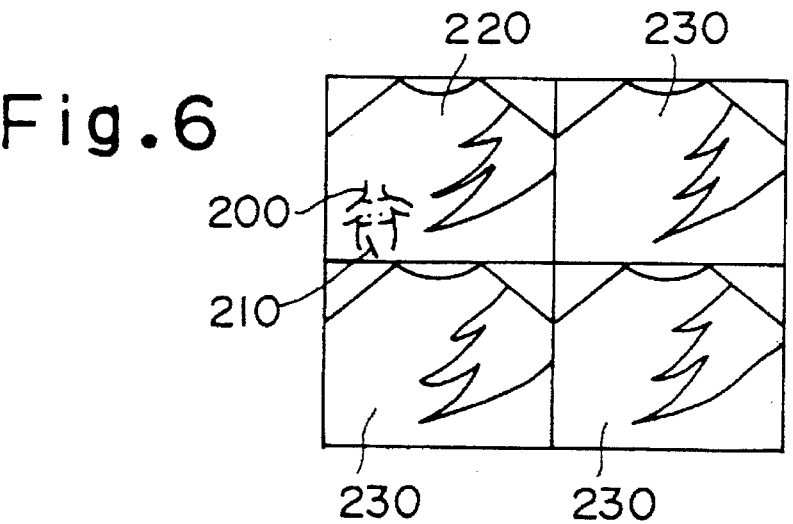
FIG. 6 is a view showing still another example of a display on a display screen of a display unit.

FIGS. 4-6 are each a view showing an example of a display on a display screen of a display unit.

In FIG. 4, a tomographic image 220 of the subject now on diagnosis is displayed throughout the screen. And a graphic image comprising a body mark 200 and a probe mark 210, and a diagnostic case 230 read out of the image memory 110 are displayed in alignment at a corner of the tomographic image 220 on an inserting basis.

In FIG. 5, the tomographic image 220 and the diagnostic case 230 are displayed with the same size in alignment of right and left. And the graphic image comprising the body mark 200 and the probe mark 210 is displayed at a corner of the tomographic image 220 on an inserting basis.

In FIG. 6, the tomographic image 220 and the graphic image comprising the body mark 200 and the probe mark 210, and in addition three diagnostic cases 230 are displayed.

While FIGS. 4-6 show three display formats by way of example, the display formats in the present invention are not to be restricted by those examples.

Further, it is noted that the present invention is not to be restricted by those in which the tomographic image 220, the diagnostic case 230 and the body mark 200 and the probe mark 210 are simultaneously displayed, and it is acceptable that those three images are sequentially individually displayed, or two of those images are simultaneously displayed.

As described above, according to the present invention, it is possible to provide an ultrasonic diagnostic apparatus permitting even an operator not skilled in the operation to perform accurately and readily estimation of the tomographic image displayed on the display screen through operation by himself, since an operation by an operator as to a display of the body mark and the probe mark permits a display of the associated diagnostic cases read out of the data base of the image memory.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An ultrasonic diagnostic apparatus comprising:

a probe to transmit ultrasonic waves inside a subject and to receive the ultrasonic waves reflected within the subject;

an operation panel to designate a body mark indicative of a diagnostic site on the subject or an internal organ of interest in the subject and a position of a probe mark indicative of the position of said probe put upon the subject;

memory means for storing image data representative of a plurality of images corresponding to the body mark and the position of the probe mark; and display means for displaying a first image based on the ultrasonic wave received by said probe from inside the subject and a second image based on the image data stored in said memory means corresponding to the body mark and the position of the probe mark, the second image including normal and abnormal diagnostic images.

2. An apparatus according to claim 1, wherein said display means simultaneously displays the body mark, the probe mark, and the second image.

3. An apparatus according to claim 2, wherein when the position of the probe mark is moved to an altered position, during a display of the second image by said display means, through an operation of said operation panel, said display means displays a third image based on the image data stored in said image memory corresponding to the altered position of the probe mark.

4. An apparatus according to claim 1, wherein said display means simultaneously displays the first image, the body mark, the probe mark, and the second image.

5. An apparatus according to claim 4, wherein when the position of the probe mark is moved to an altered position, during a display of the second image by said display means, through an operation of said operation panel, said display means displays a third image based on the image data stored in said image memory corresponding to the altered position of the probe mark.

6. An apparatus according to claim 1, wherein when the position of the probe mark is moved to an altered position, during a display of the second image by said display means, through an operation of said operation panel, said display means displays a third image based on the image data stored in said image memory corresponding to the altered position of the probe mark.

7. An apparatus according to claim 1, wherein said display means displays the second image including a plurality of normal and abnormal diagnostic images.

* * * * *